(12) United States Patent
Hwang et al.

(10) Patent No.: US 9,693,934 B2
(45) Date of Patent: Jul. 4, 2017

(54) COSMETIC TISSUE COMPRISING MICROEMULSION PARTICLES, AND PRODUCTION METHOD FOR SAME AND METHOD OF USING SAME

(71) Applicant: AMOREPACIFIC CORPORATION, Seoul (KR)

(72) Inventors: Joon Young Hwang, Yongin-si (KR); Min Kyung Shim, Yongin-si (KR); Young So Kim, Yongin-si (KR); Sang Hoon Han, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 31 days.

(21) Appl. No.: 14/353,387

(22) PCT Filed: Nov. 1, 2012

(86) PCT No.: PCT/KR2012/009123
§ 371 (c)(1),
(2) Date: Apr. 22, 2014

(87) PCT Pub. No.: WO2013/066073
PCT Pub. Date: May 10, 2013

(65) Prior Publication Data
US 2014/0271753 A1    Sep. 18, 2014

(30) Foreign Application Priority Data

Nov. 3, 2011 (KR) .................. 10-2011-0113839

(51) Int. Cl.
| | | |
|---|---|---|
| *A61K 8/02* | (2006.01) | |
| *A61K 8/06* | (2006.01) | |
| *D21H 27/00* | (2006.01) | |
| *D21H 21/52* | (2006.01) | |
| *A61Q 19/00* | (2006.01) | |
| *A61Q 19/02* | (2006.01) | |
| *D21H 21/24* | (2006.01) | |

(52) U.S. Cl.
CPC .......... *A61K 8/0208* (2013.01); *A61K 8/068* (2013.01); *A61Q 19/00* (2013.01); *A61Q 19/02* (2013.01); *D21H 21/52* (2013.01); *D21H 27/002* (2013.01); *D21H 21/24* (2013.01)

(58) Field of Classification Search
CPC ...... A61K 8/0208; A61K 8/068; D21H 21/24; D21H 21/52; D21H 27/002
USPC ...................... 424/401; 427/372.2
See application file for complete search history.

(56) References Cited

U.S. PATENT DOCUMENTS

| | | | | |
|---|---|---|---|---|
| 6,287,582 B1* | 9/2001 | Gott | ............ | A61K 8/0208 424/400 |
| 2005/0118270 A1* | 6/2005 | Moro | ............ | A61K 9/1635 424/485 |
| 2006/0134156 A1* | 6/2006 | Marion | ............ | A61K 8/0208 424/401 |
| 2006/0159637 A1* | 7/2006 | Meyer | ............ | A61K 8/0208 424/59 |
| 2008/0038330 A1* | 2/2008 | Fleischer | ............ | A61K 9/127 424/450 |
| 2010/0161029 A1* | 6/2010 | Filippini | ............ | A61K 8/066 623/1.15 |

FOREIGN PATENT DOCUMENTS

| | | |
|---|---|---|
| CN | 101633781 | 1/2010 |
| JP | 2003507406 A | 2/2003 |
| JP | 2009518559 A | 5/2009 |
| KR | 1020030079901 A | 10/2003 |
| KR | 1020030097189 A | 12/2003 |
| KR | 1020040033855 A | 4/2004 |
| KR | 100801828 B1 | 1/2008 |
| KR | 100840988 B1 | 6/2008 |
| KR | 1020100066754 A | 6/2010 |
| WO | 2010009661 | 1/2010 |

OTHER PUBLICATIONS

Chemron Corporation,Essentials of Personal Care, [online],[retrieved on Sep. 3, 2016]. Retrieved from the Internet< URL:http://www.chemicalonline.com/doc/essentials-of-personal-care-0001>.*
Chinese Office Action-Chinese Application No. 201280054092.0 dated May 4, 2015, citing CN101633781.
International Search Report with English Translation for International Application No. PCT/KR2012/009123 dated Feb. 27, 2013.
Written Opinion for International Application No. PCT/KR2012/009123 dated Feb. 27, 2013.

* cited by examiner

Primary Examiner — Janet Epps-Smith
Assistant Examiner — Courtney Brown
(74) Attorney, Agent, or Firm — Cantor Colburn LLP

(57) ABSTRACT

The present invention relates to a cosmetic tissue comprising microemulsion particles, and to a production method for same and method of using same. The present invention provides a cosmetic tissue to which is securely attached a dried composition comprising microemulsion particles of no more than 5,000 nm. Also, the present invention provides a production method for cosmetic tissue comprising: a first step of obtaining a composition comprising microemulsion particles of no more than 5,000 nm; a second step of coating the composition onto a tissue substrate; and a third step of drying the composition, and the present invention provides a method of using same. According to the present invention, after the skin has been cleaned, removal of the remaining water fraction and coating of a dermatological beauty composition are carried out in one go, thereby allowing easy-to-use and effective cosmetic enhancement to the skin.

1 Claim, 1 Drawing Sheet

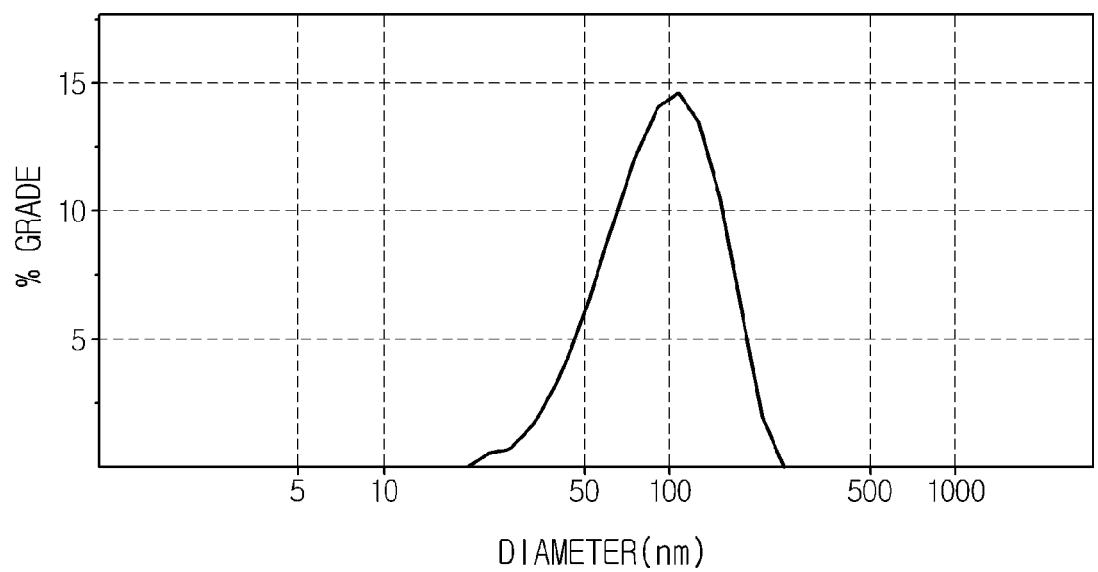

COSMETIC TISSUE COMPRISING MICROEMULSION PARTICLES, AND PRODUCTION METHOD FOR SAME AND METHOD OF USING SAME

TECHNICAL FIELD

The present invention relates to a cosmetic tissue comprising microemulsion particles, and methods for preparing and using thereof. More particularly, the present invention relates to a cosmetic tissue that is convenient to use skin and assists effective skin moisturizing because of the removal of residual moisture simultaneously with the application of a skin cosmetic composition after cleansing the skin, and methods for preparing and using thereof.

BACKGROUND ART

In general, a cosmetic composition is applied to the skin for the purpose of moisturizing, whitening and elasticizing. For example, skin-moisturizing cosmetic agents comprise water-soluble and oil-soluble moisturizing ingredients, and functional ingredients may be further added thereto to enhance the moisturizing effect. For example, Korean Laid-Open Patent No. 10-2008-0125213 discloses a skin-moisturizing cosmetic composition containing fermented extract of herb medicine materials. In addition, Korean Patent No. 10-0840988 discloses a skin-moisturizing composition containing alginic acid. Such emulsion type cosmetic agents are used in such a manner that they are taken by the user's hand in an adequate amount and applied uniformly to a desired site to allow uniform spreading of their moisturizing ingredients on the skin.

As mentioned above, according to the related art, application of skin moisturizing agents have been adopted to prevent loss of skin moisture content. However, although it is not difficult to apply such a method to local sites such as faces or hands, application of cosmetic agents to the whole parts of the user's body (whole body) is very hard and requires a long period of time. Moreover, a significantly long time is required to apply cosmetic agents to the whole body after cleansing and drying the user's body by using cotton towel or the like.

First of all, the above-described process has been regarded recently as a critical process making the skin dry. Particularly, after cleansing the skin, natural moisturizing ingredients by which the skin moisture content is maintained are wiped off by a cleaner. Herein, when moisture is removed by cotton towel or the like in the absence of natural moisturizing ingredients, the skin is in contact with dry air so that a large amount of moisture may be lost in a short time. When such a drying process is repeated every day, the skin moisture content decreases accordingly, resulting in a dry skin condition.

The above-mentioned method of applying skin moisturizing agents after cleansing the skin is not amenable to application to the whole body and requires a long period of time. Moreover, the resultant moisturizing effect is not high as compared to the above-mentioned disadvantages. First of all, when moisture is removed by cotton towel or the like in the absence of natural moisturizing ingredients after cleansing, the skin is in contact with dry air, resulting in loss of a large amount of moisture in a short time.

REFERENCES

Patent Documents

Patent Document 1: Korean Laid-Open Patent No. 10-2008-0125213
Patent Document 2: Korean Patent No. 10-0840988

DISCLOSURE

Technical Problem

A technical problem to be solved by the present invention is to provide a novel type of skin cosmetic product that realizes skin moisturizing and whitening effects more simply and effectively, and methods for preparing and using the same. More particularly, an object of the present invention is to provide a cosmetic tissue that is convenient to use and time-efficient because of the removal of residual moisture simultaneously with the application of a skin cosmetic composition and assists effective skin beauty treatment, and preparation and use thereof.

Technical Solution

In one general aspect, there is provided a cosmetic tissue in which a composition comprising microemulsion particles having a size of 5000 nm or less is dried and fixed.

In another general aspect, there is provided a method for preparing a cosmetic tissue, comprising the steps of:
 i) obtaining a cosmetic composition comprising microemulsion particles having a size of 5000 nm or less;
 ii) coating the composition onto a tissue substrate; and
 iii) drying the composition.

According to an embodiment, step i) preferably comprises: a first emulsification step of agitating a mixture comprising 0.5-50 wt % of an oil-soluble moisturizing ingredient, 0.5-30 wt % of a water-soluble moisturizing ingredient, and 0.1-10 wt % of a surfactant; and a second emulsification step of emulsifying the mixture emulsified from the first emulsification step to form microemulsion particles having a size of 5000 nm or less.

In still another general aspect, there is provided a method for using the cosmetic tissue according to the present invention, wherein the cosmetic tissue is allowed to be in contact with the skin in the presence of moisture on the skin.

Advantageous Effects

According to the embodiments of the present invention, it is possible to carry out removal of residual moisture simultaneously with application of a skin cosmetic composition, after cleansing the skin. Therefore, the cosmetic tissue is convenient to use and time-efficient. In addition, after cleansing the skin, the time during which the skin is exposed to dry air is minimized to reduce moisture loss, thereby assisting effective skin beauty treatment.

DESCRIPTION OF DRAWINGS

The FIGURE is a graph illustrating the distribution of diameters of microemulsion particles comprised in the composition prepared according to an embodiment of the present invention.

BEST MODE

As described above, methods for imparting moisturizing and whitening effects to the skin mostly comprise applying skin application compositions (cosmetic agents) to the skin by the user's hands after cleansing. However, as mentioned above, such methods comprising cleansing the body, removing moisture and drying the body by using cotton towel or the like and applying skin application compositions to the skin are not amenable to application to the whole parts of body (whole body), require a long period of time and are inconvenient. First of all, removal of moisture using cotton towel in the absence of natural moisturizing ingredients after cleansing causes skin drying. In other words, after removing moisture, the skin is in contact with dry air, resulting in loss of a large amount of moisture in a short time.

Thus, the present invention provides novel beauty treatment that imparts a skin cosmetic effect to the whole body as well as local sites of skin such as faces or hands in a simple and efficient manner. Particularly, the present invention provides a cosmetic tissue that realizes removal of moisture simultaneously with application of a skin cosmetic composition. The present invention also provides a method for preparing the cosmetic tissue and a method for using the cosmetic tissue. According to the present invention, the cosmetic tissue is convenient to use and minimizes the time during which the skin is exposed to dry air by the time of applying a skin application composition (cosmetic agent) after cleansing, thereby contributing to effective skin beauty treatment.

Hereinafter, the present invention will be explained in more detail.

The cosmetic tissue according to the present invention comprises a skin application composition. Particularly, the cosmetic tissue has a skin application composition dried and fixed therein. More particularly, the cosmetic tissue comprises a tissue substrate and a skin application composition dried and fixed in the tissue substrate. Preferably, the skin application composition is fixed over the whole area of the tissue substrate.

As used herein, the tissue substrate is not limited particularly. The tissue substrate may be any one that allows fixation of the skin application composition while providing at least water absorption property for removing moisture. The tissue substrate may be selected from pulp materials and fibrous materials (fabrics). For example, the tissue substrate may be selected from conventional tissue paters and towels. The tissue may be single-layered or double- or multi-layered and the size thereof is not limited particularly.

After the tissue substrate is (coated) impregnated with the skin application composition, the skin application composition is fixed to the tissue substrate by drying. Herein, the skin application composition fixed to the tissue substrate at least comprises microemulsion particles. There is no particular limitation in microemulsion particles, as long as they help skin beauty treatment, comprising moisturizing, whitening, elasticizing, anti-wrinkling, pore treating and antibacterial treatment. For example, the microemulsion particles comprise at least one skin moisturizing substances selected from oil-soluble moisturizing ingredients and water-soluble moisturizing ingredients. In addition, the skin application composition fixed to the tissue substrate may comprise other dry ingredients in addition to the microemulsion particles. The dry ingredients may be those added generally to conventional skin application compositions.

As mentioned above, the skin application composition comprising at least microemulsion particles are fixed to the cosmetic tissue according to the present invention in a dry state. The skin application composition restores its original state when it is wetted upon the contact with water. As used herein, the term 'restore' means that the skin application composition (comprising microemulsion particles) fixed to the tissue substrate exists in its dry state first, and is provided with the same cosmetic effects (moisturizing, whitening, etc.) as its emulsion state upon the contact with water (when the skin application composition is in contact with water by the moisture absorption of the tissue substrate). In other words, the cosmetic tissue is in contact with moisture to restore its cosmetic effect such as a moisturizing effect.

Herein, the skin application composition comprising the microemulsion particles should have coatability (impregnability) to the tissue substrate. In other words, the skin application composition should be coated uniformly over the whole area of the tissue substrate (the tissue substrate should be impregnated uniformly with the skin application composition). In addition, the skin application composition should maintain its stability after drying. In other words, the skin application composition should be stable after drying without discoloration or staining. For this, the microemulsion particles have a size of 500 nm or less. When the microemulsion particles have a size (diameter) greater than 5000 nm, the impregnability is degraded and discoloration or staining may occur after drying. In addition, in this case, the restorability is degraded, and thus it is difficult to provide a good cosmetic effect, such as a moisturizing effect.

In other words, according to the present invention, it has been found that when the tissue substrate is impregnated with the skin application composition comprising microemulsion particles, dried and fixed thereto, the size of microemulsion particles plays an important technical role. Particularly, when the microemulsion particles have a size of 5000 nm or less, the tissue substrate is impregnated with a large amount of skin application composition and high stability is maintained, thereby providing a good cosmetic effect after restoration. Considering these, the microemulsion particles preferably have a size (diameter) of 1-500 nm, more preferably a size (diameter) of 5-300 nm. Within such a preferred range, high stability and restorability are obtained, thereby providing a good moisturizing effect.

The skin application composition preferably comprises an oil-soluble moisturizing ingredient, water-soluble moisturizing ingredient, surfactant (emulsifier) and water. Particularly, the skin application composition has an oil phase and an aqueous phase, wherein the oil phase comprises an oil-soluble moisturizing ingredient and surfactant (emulsifier) and the aqueous phase comprises a water-soluble moisturizing ingredient and water. In addition, the skin application composition comprises microemulsion particles having a size of 5000 nm or less, formed from the oil-soluble moisturizing ingredient and/or water-soluble moisturizing ingredient by emulsification. Herein, water is removed by drying.

In addition, after the tissue substrate is coated (impregnated) with the skin application composition, the skin application composition is dried in a short time in view of processability and should leave no non-dried residue (liquid phase) after drying. For this, the skin application composition preferably comprises 0.5-50 wt % of the oil-soluble moisturizing ingredient and 0.5-30 wt % of the water-soluble moisturizing ingredient based on the total weight (dry weight) of the composition fixed to the tissue substrate.

Hereinafter, a method for preparing the cosmetic tissue according to the present invention will be explained in detail.

The method for preparing the cosmetic tissue according to the present invention comprises the steps of: i) obtaining a skin application composition comprising microemulsion particles having a size of 5000 nm or less; ii) coating the skin application composition onto a tissue substrate; and iii) drying the skin application composition.

In step i), the skin application composition preferably comprises an oil phase and an aqueous phase, the oil phase comprises an oil-soluble moisturizing ingredient and a surfactant (emulsifier), and the aqueous phase comprises a water-soluble moisturizing ingredient and water. The composition is subjected to emulsification to form an emulsion formulation comprising microemulsion particles. The emulsion formulation may be a type of oil in water (O/W) emulsion or water in oil (W/O) emulsion.

The oil-soluble moisturizing ingredient is not particularly limited. The oil-soluble moisturizing ingredient preferably has oil solubility in addition to a moisturizing effect, and comprises any materials used in conventional skin cosmetic agents or moisturizers. Oil-soluble moisturizing ingredients comprise liquid or solid ingredients and may be selected from hydrocarbons, alkyl esters, siloxanes and fats and oil derived from plants or animals. Particular examples of oil-soluble moisturizing ingredients comprise at least one selected from hydrogenated C6-14 olefin polymers, cetyl octanoate, hydrogenated jojoba oil, cyclomethicone, dimethicone, cyclopentasiloxane, sunflower seed oil, mineral oil, squalane, octyldodecyl myristate, olive oil, macadamia nut oil, glyceryl octanoate and castor oil.

In addition, the oil-soluble moisturizing ingredient is comprised in the skin application composition (emulsion) in an amount of 0.5-50 wt % based on the total weight of the composition. Herein, when the oil-soluble moisturizing ingredient is comprised in an amount less than 0.5 wt %, little or no skin moisturizing effect is obtained. When the oil-soluble moisturizing ingredient is comprised in an amount greater than 50 wt %, the composition may remain in a liquid phase to cause staining even after a drying step. Considering these, the oil-soluble moisturizing ingredient is comprised preferably in an amount of 5-30 wt % based on the total weigh of the skin application composition (emulsion).

Various water-soluble moisturizing ingredients may be used. In general, most moisturizing ingredients soluble in water may be used. For example, the water-soluble moisturizing ingredient may be at least one selected from higher alcohols such as glycerin, butylene glycol or propylene glycol and derivatives thereof; and alkoxylated alcohols such as polyethylene glycol and derivatives thereof, but is not limited thereto. The water-soluble moisturizing ingredient may be any one currently used in conventional skin cosmetic agents or moisturizers.

In addition, the water-soluble moisturizing ingredient is comprised in the skin application composition (emulsion) in an amount of 0.5-30 wt % based on the total weight of the composition. When the water-soluble moisturizing ingredient is comprised in an amount less than 0.5 wt %, it is not possible to obtain a sufficient moisturizing effect. When the water-soluble moisturizing ingredient is comprised in an amount greater than 30 wt %, it may adversely affect drying and restoration steps. In other words, when an excessively large amount (>30 wt %) of water-soluble ingredient is comprised, discoloration may occur after drying, staining may occur because of difficulty in drying within a short time, and a sufficient moisturizing effect cannot be obtained because of poor restorability. Considering these, the water-soluble moisturizing ingredient is comprised preferably in an amount of 5-20 wt % based on the total weight of the skin application composition (emulsion).

There is no particular limitation in the surfactant and any surfactants (emulsifiers) currently used in conventional skin cosmetic agents or moisturizers may be used. Particular examples of the surfactant comprise at least one selected from polyethylene glycol-added hydrocarbons which are alkoxylated alcohols, such as CETEARETH-12 and CETEARETH-20, ionic functional group-added hydrocarbons having a hydrophilic group, and silicone surfactants, but are not limited thereto.

In addition, the surfactant may be comprised in the skin application composition (emulsion) in an amount of 10 wt % or less based on the total weight of the composition. Particularly, the surfactant may be comprised in an amount of 0.1-10 wt %. When the surfactant is comprised in an amount less than 0.1 wt %, it is difficult to perform emulsification. When the surfactant is comprised in an amount greater than 10 wt %, it may adversely affect the drying and restoration steps and the applicability of the skin application composition may be degraded. The balance is water that may be selected from purified water and the like.

Further, the skin application composition may further comprise other additives in addition to the above-described ingredients. Such additives comprise those used in conventional skin cosmetic agents or moisturizers. Particular examples of additives comprise thickeners, antioxidants and pH modifiers.

The thickener may be selected from xanthan gum, carbomer, magnesium aluminum silicate, cellulose gum, dextrin palmitate, polyacrylate, sodium polyacrylate, hydroxypropylmethyl cellulose, cetyl hydroxyethyl cellulose, sodium magnesium silicate, acrylate/C10-30 alkyl acrylate crosspolymer, hydroxypropyl starch phosphate, polyacrylate-13, hydroxyethyl acrylate/sodium acryloyl dimethyl taurate copolymer, PET-240/HDI copolymer bisdecyltetraceth-2 ether or the like. The antioxidant may be selected from tocoperyl acetate, butylated hydroxytoluene or the like. The preservative may be selected from phenoxyethanol, methylparaben, butylparaben, propylparaben, imidazolydinyl urea, chlorphenesin or the like. The pH modifier may be selected from triethanolamine, citric acid or the like.

In addition to the above additives, the skin application composition may further comprise natural flavorings such as natural flavorings or combined flavorings, and pigments or the like. The skin application composition may further comprise a stabilizer such as a polymer for stabilization of emulsion. Such stabilizers may be those used generally in the art. In addition, a skin moisturizing composition optionally comprises an organic solvent such as alcohols and ketones.

The skin application composition, i.e., the composition comprising at least an oil-soluble moisturizing ingredient, water-soluble moisturizing ingredient, surfactant and water is formed into emulsion and further emulsified to form microemulsion particles.

Particularly, in step i), the mixture comprising the above-mentioned ingredients in the amounts as defined above is agitated so that it may be emulsified preliminarily. In other words, the mixture is emulsified homogeneously, for example, by using a homogenizer, so that emulsion particles may be formed. After the emulsification using a homogenizer, an emulsion mixture comprising macroemulsion particles is obtained.

Then, the preliminary emulsion thus obtained is further emulsified to form microemulsion particles. In other words, the preliminary emulsion mixture is further emulsified to form microemulsion particles having a size (diameter) of 5000 nm or less, thereby providing a homogeneous and stable emulsion. Various methods may be used to form microemulsion particles having a size of 5000 nm or less. Herein, the emulsification step may be carried out by using any methods capable of producing fine particles having a size of 5000 nm or less. Particular examples of such methods comprise but are not limited to a high-pressure emulsification method using a high-pressure emulsification system, phase transition temperature emulsification method using a phase transition temperature, or the like.

In addition, when carrying out further emulsification, the microemulsion particles preferably have a size (diameter) of 1-500 nm, more preferably a size (diameter) of 5-300 nm. To control the particle size within the above-defined range, various methods may be used. For example, the preliminary emulsion may be introduced to a high-pressure emulsification system under pressure control to control the particle size. More particularly, the particle size may be controlled by applying shear to the emulsion in a high-pressure emulsification system under 1000-1500 atm.

Through such further emulsification, it is possible to obtain an emulsion type skin application composition comprising microemulsion particles having a size of 5000 nm or less. Then, the skin application composition is applied to a tissue substrate (step ii)). Herein, step ii) may be carried out in such a manner that the whole area of the tissue substrate is coated with the skin application composition, for example, by using a spray coating process. Preferably, the tissue substrate is impregnated with (dipped into) the skin application composition so that the tissue substrate is wetted with the skin application composition over the whole area thereof. The whole part of the tissue substrate may be dipped into the skin application composition for a predetermined time. Herein, the amount of skin application composition incorporated to the tissue substrate may be controlled through the area, thickness and material of the tissue substrate or the composition (formulation) of the skin application composition. After the impregnation, the tissue substrate is maintained in the skin application composition for a predetermined time, taken out therefrom and is allowed to stand so that a predetermined amount of composition may be removed, followed by drying (step iii)).

In drying step iii), the tissue substrate impregnated with the skin application composition is dried to remove at least water (moisture). Drying may be carried out through any method with no particular limitation, as long as it allows water evaporation. For example, the tissue substrate impregnated with the skin application composition may be dried at a temperature of 45-120° C. for a predetermined time or dried by using a freeze drying process. The drying step is not limited as long as it allows removal of moisture.

The method for using the cosmetic tissue according to the present invention will be explained hereinafter.

The cosmetic tissue according to the present invention is used in the presence of moisture on the skin. The moisture present on the skin may be one present on the skin after cleansing the body or one formed on the skin artificially. In the presence of moisture, the cosmetic tissue according to the present invention is in contact with the skin. In other words, the skin is dried by using the cosmetic tissue according to the present invention in the same manner as using a general cotton towel.

In this manner, the moisture present on the skin is absorbed and removed by the tissue substrate while the skin application composition fixed to the tissue substrate is applied uniformly to the skin. Herein, the skin application composition fixed to the tissue substrate present originally in a dry state restores its cosmetic effect by rewetting through the contact with moisture. In other words, the skin application composition restores and imparts skin cosmetic effects such as skin moisturizing, whitening, elasticizing, anti-wrinkling, pore treating and antibacterial effects, depending on the particular formulation.

The cosmetic tissue as described above is convenient to store and use. In other words, a skin cosmetic composition may be applied to the whole parts of body (whole body) as well as local parts such as faces or hands. In addition, it is possible to minimize the time during which the skin is exposed to dry air by the time of applying the skin cosmetic composition. Particularly, it is possible to carry out removal of moisture simultaneously with application of a skin cosmetic composition after cleansing, thereby minimizing the time during the skin is exposed to dry air and reducing moisture loss. As a result, it is possible to carry out effective skin beauty treatment, such as skin moisturizing. As described above, the cosmetic tissue shows high stability and good applicability without staining caused by non-dried liquid.

MODE FOR INVENTION

Examples and Comparative Examples now will be described. The following Examples are for illustrative purposes only and not intended to limit the scope of the present invention.

Example 1

A skin moisturizing composition (emulsion formulation) is obtained by using the ingredients as shown in the following Table 1 through the following steps (1)-(5). Herein, 10 wt % of oil-soluble moisturizing ingredients and 10 wt % of water-soluble moisturizing ingredients are comprised in the total weight of the composition, and the ingredients are emulsified by using a homogenizer, and then micro-emulsified by using a high-pressure emulsification system to form nano-sized microemulsion particles.

<Preparation Method>

(1) Aqueous phase ingredients are mixed and dissolved under heating to 70° C.
(2) Oil-phase ingredients are mixed and dissolved under heating to 70° C. in a separate container.
(3) The oil-phase mixture of step (2) is introduced to the aqueous phase mixture of step (1) and the resultant mixture is emulsified by using a homogenizer.
(4) The mixture emulsified from step (3) is further emulsified by using a high-pressure emulsification system. As a high-pressure emulsification system, a microfluidizer is used and shear force is applied to the mixture under a pressure of 1200 atm.
(5) The mixture emulsified from step (4) is cooled to 30° C.

The diameter distribution of the emulsion particles contained in the emulsion formulation obtained according to Example 1 is determined by using Zetasizer (Malvern) and the results are shown in the FIGURE in the form of a graph. As shown in the FIGURE, the emulsion particles contained in the emulsion formulation according to Example 1 have a diameter ranging from 20 nm to 200 nm, and thus are distributed uniformly within a nanosize range.

Comparative Examples 1 to 3

Skin moisturizing compositions (emulsion formulations) are obtained in the same manner as Example 1, except that Comparative Example 1 is carried out by using a conventional emulsification method using a homogenizer only with no high-pressure emulsification step. The emulsion formulation according to Comparative Example 1 has a particle size distributed within a range of about 10 μm-120 μm.

In Comparative Example 2, an emulsification formulation comprising nano-sized emulsion particles is obtained in the same manner as Example 1 by using a high-pressure emulsification step, except that the oil-soluble moisturizing ingredient is comprised in an amount of 55 wt %.

In Comparative Example 3, an emulsification formulation comprising nano-sized emulsion particles is obtained in the same manner as Example 1 by using a high-pressure emulsification step, except that the water-soluble moisturizing ingredient is comprised in an amount of 40 wt %.

TABLE 1

<Composition of emulsification formulation>

| | Ingredients | | Ex. 1 (wt %) | Comp. Ex. 1 (wt %) | Comp. Ex. 2 (wt %) | Comp. Ex. 3 (wt %) |
|---|---|---|---|---|---|---|
| Aqueous phase | Water | Purified water | to 100 | to 100 | to 100 | to 100 |
| | Water-soluble moisturizing ingredient | Glycerin | 5 | 5 | 5 | 20 |
| | | Butylene glycol | 5 | 5 | 5 | 20 |
| | Preservative | Phenoxyethanol | 0.5 | 0.5 | 0.5 | 0.5 |
| Oil phase | Oil-soluble moisturizing ingredient | Hydrogenated C6-14 olefin polymer | 3 | 3 | 15 | 3 |
| | | Cetyl octanoate | 3 | 3 | 15 | 3 |
| | | Hydrogenated jojoba oil | 3 | 3 | 15 | 3 |
| | | Cyclomethicone | 1 | 1 | 10 | 1 |
| | Surfactants | Ceteareth-20 | 1.5 | 1.5 | 1.5 | 1.5 |
| | | Ceteareth-12 | 1.5 | 1.5 | 1.5 | 1.5 |

Test Example 1

The tissue impregnability of each of the emulsion formulations according to Example 1 and Comparative Examples 1-3 is determined as follows.

A tissue having the same size (20 cm×20 cm) and same weight (2 g/20 cm×20 cm) is impregnated with the same amount (10 g) of each of the emulsions according to Example 1 and Comparative Examples 1-3, and the tissue is evaluated whether it is impregnated uniformly with each emulsion or not. The total area of each tissue is divided equally into 9 portions, the area impregnated within the same time is measured for each portion, and the results are shown in the following Table 2.

TABLE 2

<Impregnability of Emulsion Formulation to tissue>

| | Area Impregnated with Emulsion (Wet portion area/Total area) |
|---|---|
| Example 1 | 9/9 |
| Comp. Ex. 1 | 4/9 |
| Comp. Ex. 2 | 6/9 |
| Comp. Ex. 3 | 7/9 |

As shown in Table 2, impregnability varies with the composition and emulsion particle size of emulsion. In the case of emulsion of Example 1 containing fine nano-sized emulsion particles, the tissue is impregnated totally with the emulsion within a short time because of low viscosity and rapid diffusion. However, in Comparative Example 1, such large emulsion particles are not diffused well. In addition, in Comparative Examples 2 and 3, the use of an excessively large amount of oil-soluble ingredients or water-soluble ingredients makes diffusion difficult.

Test Example 2

The stability of each emulsion with which the tissue is impregnated is evaluated after drying. In addition, the emulsion is evaluated to determine whether or not it is dried well to allow storage and use after drying.

First, the tissue is impregnated with each of the emulsion formulations according to Example 1 and Comparative Examples 1-3, and then is dried under the same conditions in a constant-temperature bath at 45° C. for 30 hours. Then, each dried sample is stored under a constant-temperature condition at 30° C. and 45° C. for 4 weeks, and then the surface condition of each sample is observed and evaluated by the naked eyes. In addition, variations in weight before and after drying are determined. Further, a dry sheet of paper is stacked on the surface of each dried sample to determine whether the paper is stained with liquid or not. The results are shown in the following Table 3.

TABLE 3

<Stablility of emulsion and dried condition of tissue after drying>

| | Stability (Constant-temperature Bath, stored for 30 hours) | | Dried condition | |
|---|---|---|---|---|
| | | | Variations in | |
| | 30° C. | 45° C. | weight | Paper test |
| Example 1 | Good | Good | −7.8 g | Good |
| Comp. Ex. 1 | Good | Discolored, staining | −7.0 g | Good |
| Comp. Ex. 2 | Good | Good | −5.4 g | Stained |
| Comp. Ex. 3 | Discolored | Discolored | −5.9 g | Stained |

As shown in Table 3, Examples 1 shows good stability at high temperature and a good dry condition with no paper staining. However, Comparative Examples 2 and 3 are not dried completely and remain still in a wet condition to cause paper staining.

Test Example 3

The following test is carried out to evaluate whether or not each tissue having emulsion dried and fixed therein is rewetted with moisture and restores its moisturizing effect. In addition, practical applicability (moisturizing effect) of each tissue as skin moisturizing cosmetic tissue is evaluated as follows.

First, the restorability test is carried out by wetting each of the tissue samples of Examples 1 and Comparative Examples 1-3 having emulsion fixed thereto through the impregnation and drying steps, squeezing water from each tissue sample to collect the same amount of liquid, drying each tissue again, and measuring the dry weight of each sample. In addition, practical applicability is determined by a panel test method, wherein five panels are allowed to use each tissue right after cleansing the skin, and evaluate the satisfaction (moisturizing effect) by rating each tissue on a scale of 1 to 10. The results are shown in the following Tables 4 and 5.

TABLE 4

<Restorability Test>

| | Dried weight (Redrying after rewetting) |
|---|---|
| Example 1 | 2.1 g |
| Comp. Ex. 1 | 1.3 g |
| Comp. Ex. 2 | 1.6 g |
| Comp. Ex. 3 | 1.9 g |

TABLE 5

<Applicability Test>

| Subjects | Ex. 1 | Comp. Ex. 1 | Comp. Ex. 2 | Comp. Ex. 3 |
|---|---|---|---|---|
| 1 | 9 | 5 | 2 | 4 |
| 2 | 7 | 6 | 2 | 4 |
| 3 | 10 | 6 | 4 | 3 |
| 4 | 10 | 8 | 5 | 7 |
| 5 | 9 | 7 | 3 | 3 |
| Average | 9.0 | 6.4 | 3.2 | 4.2 |

As shown in Table 4, Example 1 shows the highest dried weight (2.1 g) in the restorability test after rewetting. This suggests that Examples 1 comprises a large amount of ingredients having a moisturizing effect even after rewetting, and thus can deliver the largest amount of moisturizing ingredient to the skin after the contact with moisture. As shown in Table 5, in the applicability (moisturizing effect) test after the practical use, Example 1 provides a higher rating as compared to Comparative Examples 1-3.

The invention claimed is:

1. A method for using a cosmetic tissue, wherein the cosmetic tissue is allowed to be in contact with the skin in the presence of moisture on the skin, wherein the method comprises using the cosmetic tissue in removal of residual moisture after cleansing skin simultaneously with application of the composition, wherein the cosmetic tissue comprises a composition in a form of microemulsion particles having a size of 20 nm to 200 nm which is dried and fixed, wherein the composition consists of water, 5-30 wt % of an oil-soluble moisturizing ingredient, 5-20 wt % of a water-soluble moisturizing ingredient, and 0.1-10 wt % of a surfactant, wherein the oil-soluble moisturizing ingredient consists of hydrogenated C6-C14 olefin polymer, cetyl octanoate, hydrogenated jojoba oil, and cyclomethicone, the water-soluble moisturizing ingredient consists of glycerin and butylene glycol, and the surfactant consists of ceteareth-20 and ceteareth-10.

\* \* \* \* \*